United States Patent [19]

Tong

[11] Patent Number: 6,141,094
[45] Date of Patent: *Oct. 31, 2000

[54] SENSITIVE LASER SPECTROSCOPIC DETECTION BASED ON THREE-DIMENSIONAL NONLINEAR FOUR-WAVE MIXING

[75] Inventor: William G. Tong, San Diego, Calif.

[73] Assignee: San Diego State University Foundation, San Diego, Calif.

[*] Notice: This patent issued on a continued prosecution application filed under 37 CFR 1.53(d), and is subject to the twenty year patent term provisions of 35 U.S.C. 154(a)(2).

[21] Appl. No.: 09/399,930

[22] Filed: Sep. 21, 1999

Related U.S. Application Data

[60] Provisional application No. 60/116,524, Jan. 20, 1999.

[51] Int. Cl.$^7$ .............................. G01J 3/02; G01N 21/74
[52] U.S. Cl. ............................................ 356/300; 356/312
[58] Field of Search .................................... 356/300, 326, 356/328, 312

[56] References Cited

U.S. PATENT DOCUMENTS 5,600,444  2/1997  Tong ........................................ 356/432

OTHER PUBLICATIONS

"Sensitivie Capillary–Based On–Column Detection Method By Laser Wave Mixing", Sandrine Berniolles, et al., Dept. of Chem., SDSU, SPIE vol. 2980, (1997) pp. 127–132,.

"Optical Fiber–Based Wave–Mixinig Probe", Jon Nunes, et al., Dept. of Chem., SDSU, SPIE vol. 2980, (1997) pp. 429–433.

"Circular Dichroism Spectroscopy Using Coherent Laser–Induced Thermal Gratings", David W. Neyer, et al., 1997 American Chemical Society, vol. 119, pp. 8293–8300.

"Optical Fiber–Based Wave Mixing as a Convenient and Sensitive Laser Analytical Tool for Condensed–Phase Analytes", Jon A. Nunes, et al., Dept. of Chem., SDSu, vol. 52, No. 5, 1998, pp. 763–769.

"Advanced Technologies for Environomental Monitoring and Remediation", Tuan Vo–Dinh, SPIE, vol. 2835, 1996, pp. 248–254.

"Circular Dichroism Spectroscopy by Four–Wave Mixing Using Polarization Grating–Induced Thermal Gratings", Jon A. Nunes, et al., Dpt. of Chem., SDSU, vol. 101, No. 18, The Journal of Physical Chemistra A, pp. 3279–3283.

"Sensitive absorbance detection method for capillary electrophoresis based on laser wave–mixing", Zhiquiang Wu, et al., Journal of Chromatography, (1997), pp. 291–298.

*Primary Examiner*—F. L. Evans
*Attorney, Agent, or Firm*—Fish & Richardson P.C.

[57] ABSTRACT

Devices and techniques for performing highly-sensitive spectroscopic measurements in a sample vapor by using a four-wave-mixing optical system and an atomizer chamber. One embodiment of a spectrometer comprises a gas-phase atomizer having an atomizer chamber operable to vaporize a sample solution to produce a sample vapor, first and second alignment templates having apertures to align a probe beam, first and second pump beams to form a four-wave mixing configuration, a laser tunable to generate a laser beam at a desired wavelength corresponding to an absorption line in the sample vapor, and a set of optical elements disposed relative to the laser and the atomizer to split the laser beam into the probe beam, the first pump beam, and the second pump beam. The probe beam, the first and second pump beams are directed to overlap with one another in the sample vapor to produce a signal beam through a four-wave mixing process.

25 Claims, 5 Drawing Sheets

SENSITIVE LASER SPECTROSCOPIC DETECTION BASED ON THREE-DIMENSIONAL NONLINEAR FOUR-WAVE MIXING

CLAIM OF PRIORITY

This application claims priority under 35 U.S.C. §119(e) to U.S. patent application Ser. No. 60/116,524, filed Jan. 20, 1999.

TECHNICAL FIELD

This application relates to detection of minute substances, and more specifically, to spectroscopic detection techniques based on nonlinear four-wave mixing in optical media.

BACKGROUND

Four-wave mixing is a process in an optical medium where three coherent optical waves interact with one another through nonlinear coupling to produce a fourth coherent signal wave. The third-order nonlinear susceptibility of the medium primarily contributes to such nonlinear coupling. The signal wave includes information on optically-excited atoms or molecules present in the medium where the three input optical waves intersect and hence can be collected to extract information about the medium. For example, the signal strength of the signal wave is associated with the population of atoms or molecules and the spectral characteristics of the signal wave can be analyzed to reveal the structure of the atoms or molecules of interest. The coherent characteristics of the four-wave mixing signal beam have a number of advantages, including a laser-like signal beam, efficient signal collection, excellent spatial resolution, and sub-Doppler spectral resolution. Hence, four-wave mixing has been widely used as a highly sensitive tool in spectroscopic measurements and many other applications requiring detection of a minute amount of a substance.

One commonly-used four-wave mixing process is the backward-scattering degenerate four-wave mixing where three input beams (two pump beams and one probe beam) are at a common frequency. The nonlinear wave mixing produces a fourth signal beam at the same common frequency as the input beams. In a two-dimensional configuration, the wave vectors of the three input beams are in the same plane when mixed inside the medium. Due to conservation of momentum, the wave vector of the generated signal beam is also in the same plane. When two pump beams counter propagate and the probe beam intersects the pump beams at a small angle (e.g., less than 1 degree), the resulting signal beam is a time-reversed replica of the probe beam and propagates in the opposite direction of the probe beam. A beam splitter can be used to separate the signal beam from the path of the probe beam for signal detection. In a three-dimensional configuration, the pump beams may be in the same plane and the probe beam may be in a different plane. Hence, the generated signal beam will not retrace the probe beam and can be directly collected by a photodetector without using a beam splitter. This increases the signal strength of the received signal and improves the signal-to-noise ratio.

The above four-wave mixing detection can be used to form a spectroscopic analyzer by coupling a four-wave mixing optical module to an atomizer. This spectroscopic analyzer can be used to analyze gas-phase, liquid-phase, and solid-phase samples. The atomizer vaporizes an analyte to produce a vapor sample and the four-wave mixing optical module performs optical measurements of the vapor sample. Such a spectroscopic analyzer may be used in a range of applications, including trace-concentration analysis using gas-phase atomizers with sample cells, circular dichroism spectroscopy, capillary electrophoresis, and liquid chromatography in various fields such as biotechnology, environmental, material engineering and science, and basic scientific research.

SUMMARY

The invention includes an optical spectrometer based on optical nonlinear four-wave mixing to achieve a high detection sensitivity of measuring minute substances with a concentration on the order of one part per $10^{15}$ or less. One embodiment of the spectrometer comprises a gas-phase atomizer having an atomizer chamber operable to vaporize a sample solution to produce a sample vapor, first and second alignment templates having apertures to align a probe beam, first and second pump beams to form a four-wave mixing configuration, a laser tunable to generate a laser beam at a desired wavelength corresponding to an absorption line in the sample vapor, and a set of optical elements disposed relative to the laser and the atomizer to split the laser beam into the probe beam, the first pump beam, and the second pump beam. The probe beam, the first and second pump beams are directed to overlap with one another in the sample vapor to produce a signal beam through a four-wave mixing process.

The gas-phase atomizer includes an atomizer chamber that has a first optical window to receive the probe beam and the first pump beam, and a second optical window opposing the first optical window to receive the second pump beam. The atomizer chamber may include a top wall and a bottom wall where the sample solution is injected and vaporized towards the top wall. The apertures of first and second alignment templates may be so arranged and positioned that the probe beam, the first and second pump beams overlap in a region is closer to the top wall than the bottom wall so as to reduce light scattering.

The first and second alignment templates may be respectively disposed near the first and second windows of the atomizer chamber to respectively have opaque plates that each have at least three apertures positioned relative to one another to define optical paths of the probe beam, first and second pump beams, and signal beam. The probe beam may form an acute angle of less than about 20 degrees with the first pump beam and be outside a plane defined by the first and second pump beams. The apertures in each alignment template are sized to make a volume formed by the overlapped probe beam, first and second pump beams less than a volume occupied by the sample vapor within the atomizer chamber. The first and second alignment templates may be symmetrically located with respect to a location where the probe beam, the first and second pump beams overlap and a pattern of the apertures in the first alignment template is a center reverse image of a pattern of the apertures in the second alignment template.

This disclosure also discloses a method for performing spectroscopic measurements by using optical nonlinear four-wave mixing. First, a sample solution is prepared to include particles of a sample to be measured. Second, the sample solution is injected into an atomizer chamber of a gas-phase atomizer to vaporize the sample solution and to produce a sample vapor. Next, a probe beam, a first pump beam, and a second pump beam are produced to be coherent with one another and are in resonance with an absorption transition in the sample. Two alignment templates are placed on both sides of the atomizer chamber to align the input beams and to block background light in the path of the signal beam. Each template has at least three apertures to align the probe beam, the first pump beam, and the second pump beam to cross and overlap with one another in the sample vapor within the atomizer chamber to produce a signal beam by optical nonlinear four-wave mixing. The probe beam forms an acute angle of less than about 20 degrees with respect to the first pump beam and may be outside a plane defined by the first and second pump beams and the pump beam. Finally, the signal beam is detected to extract spectroscopic and chemical information of the sample.

The details of one or more embodiments of the disclosure are set forth in the accompanying drawings and the description below. Other features, objects, and advantages will be apparent from the description and drawings, and from the claims.

DESCRIPTION OF DRAWINGS

Like reference numbers and designations in the various drawings indicate like elements.

DETAILED DESCRIPTION

Figure 1:
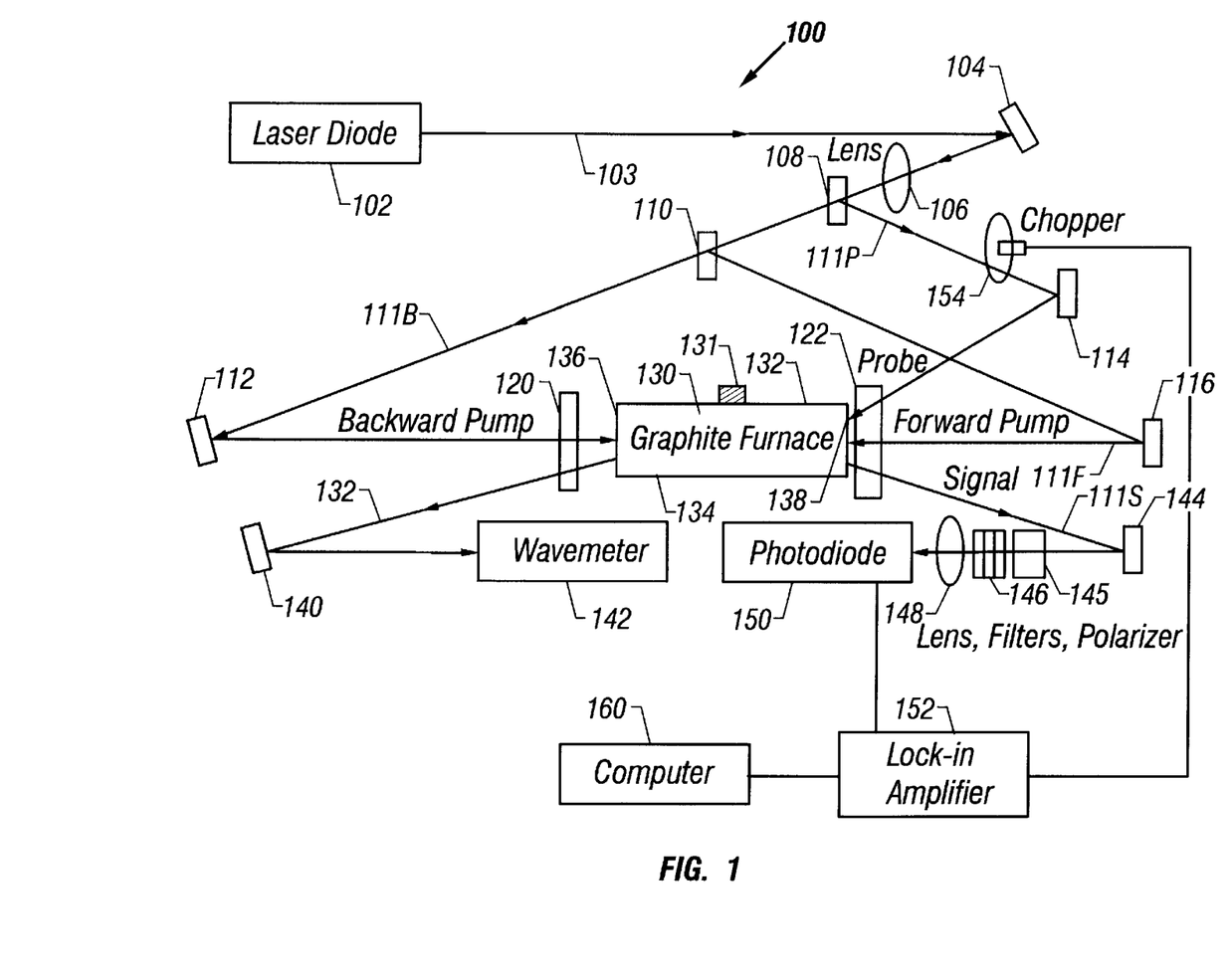
FIG. 1 shows one embodiment of an optical spectrometer based on four-wave mixing.

FIG. 1 schematically shows one embodiment 100 of a four-wave-mixing gas-phase spectroscopic analyzer. A laser 102, e.g., a diode laser, produces a tunable coherent beam 103. The laser 102 is tuned to a desired wavelength in resonance with a selected spectral line of a sample under measurement. A mirror 104 and a lens 106 guide the beam 103 to beam splitters 108 and 110. The beam splitter 108 reflects a portion of the beam 103 as a probe beam 111P and transmits the remaining part of the beam 103 to the beam splitter 110. The beam splitter 110 produces a forward pump beam 111F by reflection and a backward pump beam 111B by transmission. Mirrors 112, 114, and 116 are positioned to respectively guide the backward pump beam 111B, the probe beam 111P, and the forward pump beam 111F so that they cross and overlap with one another. The probe beam 111P and the forward pump beam 111F cross each other to form an acute angle. A gas-phase atomizer 130, e.g., a graphite furnace electrothermal atomizer, is used to produce a vapor sample in a location where the beams overlap. The atomizer 130 has a chamber with a top wall 132 and a bottom wall 134, and two side windows 136 and 138 for receiving optical signals. A sample is resolved in a solvent which is injected from an injection port 131 on the top wall 132 into the atomizer 130. The injected liquid drops to the bottom wall 134 and becomes vaporized. A computer 160 is included in the analyzer 100 to process and store signals from the photodetector 150. The computer 160 may also function as a system controller to control operations of the atomizer 130 or the laser 102.

The probe beam 111P, the forward pump beam 111F, and the backward pump beam 111B as shown form a three-dimensional, non-planar, four-wave-mixing configuration. The probe beam 111P is in a different plane than the plane defined by the pump beams 111F and 111B. When two input beams intersect at a small angle in an optical medium, constructive and destructive interferences of these beams form periodic modulation in the medium. Two of the three input beams write a grating inside the graphite furnace, and the third input beam scatters off the grating to produce the fourth coherent signal beam 111S. The difference between ground- and excited-state populations across the modulation or gratings depends on the excitation wavelength and the angle between the grating-writing beams. The signal beam 111S is generated in an optical path different from the probe beam 111P and can be directly collected by a photodetector 150 (e.g., a photodiode). A detection module 142 is also positioned relative to the furnace chamber 130 to receive the transmitted probe beam 132 and measures certain properties of the transmitted probe beam 132. For example, the detection module 142 may include a wavemeter to measure the wavelength of the probe beam for spectroscopic analysis.

Figure 2:
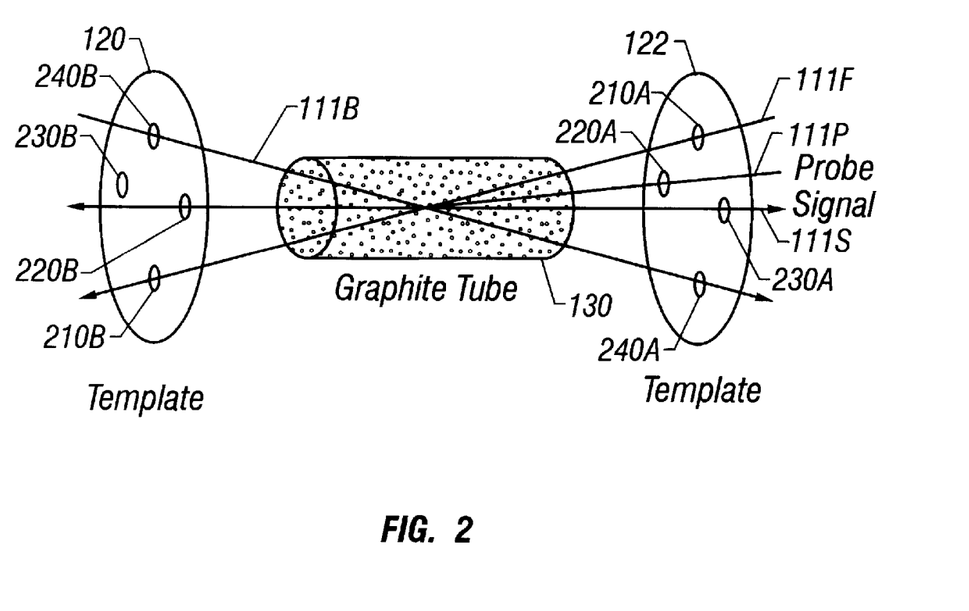
FIG. 2 illustrates one configuration of the alignment templates that align the input beams to an atomizer chamber.

Two alignment templates 120 and 122 are respectively placed on two sides of the furnace chamber 130 for pre-alignment of the three input beams 111P, 111F, and 111B. FIG. 2 shows one embodiment of the alignment templates 120 and 122. Each alignment template may be an opaque mask having at least three specially designed holes for transmitting beams. Thus, templates 120 and 122 also serve as spatial filters to prevent the scattered background light from reaching the detector 150. The templates 120 and 122 may be made by simply forming four small holes, one for each beam involved in a four-wave mixing process, in two thin aluminum plates. The pattern formed by the holes in one template is inversely symmetric with respect to the pattern formed by the holes in another template. In FIG. 2, the templates 122 and 120 have holes 210A, 220A, 230A, 240A and 210B, 220B, 230B, 240B, respectively. The templates 122 and 120 are positioned relative to the furnace chamber 130 so that holes 210A and 210B define the path of the forward pump 111F, holes 220A and 220B define the path of the probe 111P, holes 230A and 230B define the path of the signal beam 111S, and holes 240A and 240B define the path of the backward pump 111B. The positions of holes 230A and 230B can be determined based on given directions of beams 111F, 111B, and 111P according to the vector conservation requirement of the four-wave mixing process. The pump beams 111F and 111B may be opposing each other, where the beam 111F goes through the holes 210A and 210B and the beam 110B goes through the holes 240B and 240A. When the beams 111F and 111B are counter propagating, they go through the same pair of holes.

The positions of the templates 120 and 122 are fixed relative to each other for a desired four-wave mixing configuration. The chamber of the gas-phase atomizer 130 may be adjusted to change its position relative to the templates 120 and 122 so the laser beams can cross and overlap in a desired position within the chamber. The relative position of a hole relative to other holes in each template is selected so that the four beams 111F, 111B, 111P, and 111S overlap in a common volume with desired crossing angles with respect to one another at a desired spacing between two templates 120 and 122. The common volume is positioned within the furnace chamber 130 at where the sample vapor is located. Preferably, the forward pump beam 111F and the probe beam 111P form an acute crossing angle of less than about 20°, more preferably less than 10°, and most preferably, less than 5°. This crossing angle is important since it affects the sharpness of gratings formed in the sample, the grating periods, and the grating washout due to thermal motion. The dimension of the holes is selected to control the beam size and also determines the volume of the overlap region at a given crossing angle between the beams 111F and 111P. The volume of the beam overlap region is adjustable and is usually smaller than the volume of the sample vapor produced in the furnace 130 so that the entire beam overlap volume is within the vapor volume. The dimension of the holes may be further adjusted to filter out the background noise in the signal beam 111S to achieve a desired signal-to-noise ratio.

Once the templates 120 and 122 are placed at their desired positions at both ends of the furnace 130, the optical components then can be pre-aligned. For example, the prealignment can be accomplished by using a visible alignment laser beam to produce four alignment beams to respectively trace the paths of beams 111F, 111B, 111P, and 111S. Thus, the first and second alignment templates 120 and 122 can be aligned in their desired positions relative to the chamber 130. Other beam guiding elements and the elements in the path of the signal beam 111S (e.g., detector 150) can also be aligned. Upon completion of the prealignment, the actual pump beams 111F and 111B and the probe beam 111P can be generated to trace the alignment beams. Therefore, implementation of templates 120 and 122 significantly simplifies the otherwise time-consuming optical alignment and optical maintenance of the system. This is especially important when using atomizers that do not fire continuously, and hence, the signal 111S is not continuously present. Thus, the optical alignment in general cannot be performed conveniently by using the generated four-wave mixing signal 111S during the transient period when the sample vapor exists.

Referring back to FIG. 1, the spectrometer 100 may also include a polarizer 145, an optical bandpass filter 146, and a lens 148 in the optical path of the signal beam 111S. These components and the photodetector 150 can be pre-aligned by using an alignment beam, preferably visible, to trace the path of the signal beam 111S. The optical filter 146 is configured to transmit light at the signal wavelength and block light at other wavelengths such as the white light emitted from the graphite furnace 130. The polarizer 145 is aligned to have its polarization substantially parallel to the signal polarization to provide polarization discrimination. The polarizer 145 may also be used to implement polarization modulated detection techniques to increase the signal-to-noise ratio in the signal detection. When all three input beams are vertically polarized, for example, the signal beam 111S is vertically polarized; when one of the three input beams 111F, 111B, and 111P is orthogonally polarized relative to the other two input beams, the signal beam 111S is orthogonally polarized. Polarization properties of laser wave mixing can be advantageously used for many important applications including sensitive circular dichroism spectroscopy. In addition, the polarizer 145 blocks randomly-polarized background light from reaching the detector 150.

The spectrometer 100 can be operated in either a continuous sampling mode or a pulsed sampling mode. In the continuous sampling mode, the laser 102 produces a continuous wave beam 103. Hence, the signal 111S is also continuous. A lock-in amplifier 152 and a chopper 154 can be used to modulate one of the input beams (e.g., the probe beam 111P) in order to increase the signal-to-noise ratio. When the laser 102 is a pulsed laser, analyzer 100 operates in the pulsed sampling mode and a "boxcar" averager may be used to replace the lock-in amplifier. In either mode of operation, the total intensity of the beams 111F, 111B, and 111P is preferably at or close to the saturation intensity of the sample to achieve an efficient four-wave mixing. The saturation intensity generally varies from one sample to another depending on properties of the excited atomic or molecular transition in the sample. When the total intensity is above the saturation intensity of a sample, the efficiency of the wave mixing decreases and other adverse effects arise, including power broadening of the spectral line that reduces the spectral resolution. In addition, the laser 102 may be configured to produce a narrow linewidth to achieve a high spectral resolution in the sub-Doppler range since the counter-propagating configuration of the pump beams 111F and 111B essentially eliminates Doppler broadening. Further, the frequency of the laser 102 may be stabilized to avoid mode hopping and to further improve the spectral resolution and the signal-to-noise ratio. Preferably, the linewidth of the laser 102 is stabilized at about a few MHZ (e.g., 1 MHz).

One implementation of the atomizer 130 is a graphite furnace electrothermal atomizer 130 for gas-phase studies at trace concentration levels. Graphite furnace detection limits are generally better than those of flame- and ICP-based conventional spectrometric methods. Graphite furnace also offers many advantages including convenient, fast, automated introduction of different types of samples, small sample size requirements, clean atomization environment, and effective use of matrices and modifiers to minimize interferences and optimize detection sensitivity. The graphite furnace electrothermal atomizer provides high sensitivity, small injection volumes, convenient sample introduction, automated programmable experimental controls, clean reducing atomization environment, and minimum background noise. The laser wave-mixing optical setup can be easily interfaced to many commercial graphite furnace systems for conventional atomic absorption spectrometers. The graphite furnace atomizer may be configured to operate based on drying, ashing and atomization stages. The drying stage evaporates the solvent, and the ashing stage further removes other remaining residues. Chemical matrix modification drastically helps remove unwanted residues and preserves the analytes for atomization in the final atomization stage. One chemical matrix modification uses a properly selected solvent or other chemical substance as an ionization suppressor to prevent atoms of molecules of a sample from ionizing during the drying stage. The ionization suppressor can ionize more readily than the analyte of interest, and hence, can flood the furnace chamber 130 with electrons so that ionization of the analyte is reduced. The wave-mixing signal is generated during the atomization stage which may last a few seconds. An inert gas (e.g., the argon gas at 20 psi) may be used to flush out unwanted residues during these stages and thus prevent oxidation.

The properties of the laser 102 in the spectrometer 100 of FIG. 1, such as the type of the laser, the laser wavelength and the laser power, may vary depending on the type of sample solutions under measurement. For example, when a Rb vapor is studied, the laser 102 may be a laser diode emitting at 780 nm with a low output power (e.g., about 22 mW to produce 14 mW at the atomizer 130). The furnace chamber 130 may be a graphite furnace from a commercial graphite furnace system, e.g., Model GTA96 from Varian Australia Pty. Ltd. The laser diode may be cooled at 4.3° C. inside a temperature-controlled laser diode mount (e.g., Model LDM-4407 ILX Lightwave Corp.) and flushed with nitrogen gas in order to prevent condensation at low temperatures. The laser diode can be driven by a temperature controller (e.g., Model LDT-5910B from ILX Lightwave Corp.) and a low-noise current controller (e.g., Model LDX-3620 from ILX Lightwave Corp.). The laser wavelength is tunable around 780 nm by controlling the temperature and/or the driving electrical current of the laser diode. To reduce the background noise and to prevent the graphite furnace power supply from affecting the laser stability, the current controller is operated by using a built-in low-noise battery instead of AC power. The laser diode wavelength is measured by using a high-resolution wavemeter (e.g., Model WA-20 from Burleigh Instruments). Laser power measurements are made using a low power laser detector (e.g., PM3 from Molectron).

The lens 106 is so positioned that its translational movement can change the beam waist of all three input beams 111F, 111B, and 111P inside the chamber 130, and thus, change the illuminated volume within the chamber 130. The forward, backward, and probe beam intensities may be about 5.5 mW, 2.7 mW, and 6.0 mW, respectively. The laser power is distributed among the three input beams so that the intensity levels of the forward pump beam 111F and the probe beam 111P are stronger than the backward pump beam 111B. The intensity of the probe beam 111P may be modulated by using an optical chopper (e.g., SR540 from Stanford Research Systems). The photodetector 150 may be an amplified photodiode (e.g., PDA50 by Thorlabs) that is placed inside a Faraday cage to reduce electrical noise. The lock-in amplifier 152 may be a DSP lock-in amplifier SR810 by Stanford Research Systems and set at a time constant of 100 ms.

Rubidium stock solutions may be prepared to evaluate the performance of the above system by dissolving RbCl in 0.1% $HNO_3$ solutions (doubly deionized water), and then diluted to prepare ppt- and ppq-level analyte solutions. It is determined that 0.1% $HNO_3$ solvent may be used to achieve a high detection sensitivity for rubidium. The total injection volume within the atomizer may be about 20 $\mu$L (i.e., 10 $\mu$L analyte and 10 $\mu$L $HNO_3$ blank).

The rubidium $D_2$ resonance line 5s $^2S_{1/2}$ –5p $^2P_{3/2}$ at 780 nm has a relatively strong absorption oscillator strength at a value of 0.67. For the particular laser diode used, a current-temperature combination at about 4.2° C. and 63.5 mA is found to provide a tunable laser output across the Rb line with good stability and minimal mode hopping. The wavelength is tuned continuously by varying the driving current of the laser diode at a constant temperature of about 4.2° C. Using graphite furnace atomization the maximum absorption wavelength for Rb is monitored on a wavemeter at 12816.4 $cm^{-1}$ (780.249 nm).

The wave-mixing signal peak generated by the graphite furnace is verified by injecting a few blanks and monitoring the blank peaks after each analyte injection. The blank is the same blank solvent matrix used to prepare the analyte solution so that the signal detected from a blank injection represents the background level. It is important to make certain that all memory effects are eliminated by firing a few blanks and monitoring the background level. If the blank peak is unusually high, a memory effect may be present due to the accumulation of analyte residues inside the graphite tube. Some memory effect can be observed when analyte concentration is high (e.g., greater than 10 parts-per-trillion) or when analyzing some elements of low volatility, especially if the atomization temperature and timing are not optimized to ensure complete elimination of analyte and matrix residues after each injection. At the very high analyte concentration range (i.e., >1 parts-per-million), it is especially important to use a high-temperature tube cleaning procedure between analyte runs to ensure complete elimination of analyte residues inside the graphite tube.

Figure 3:
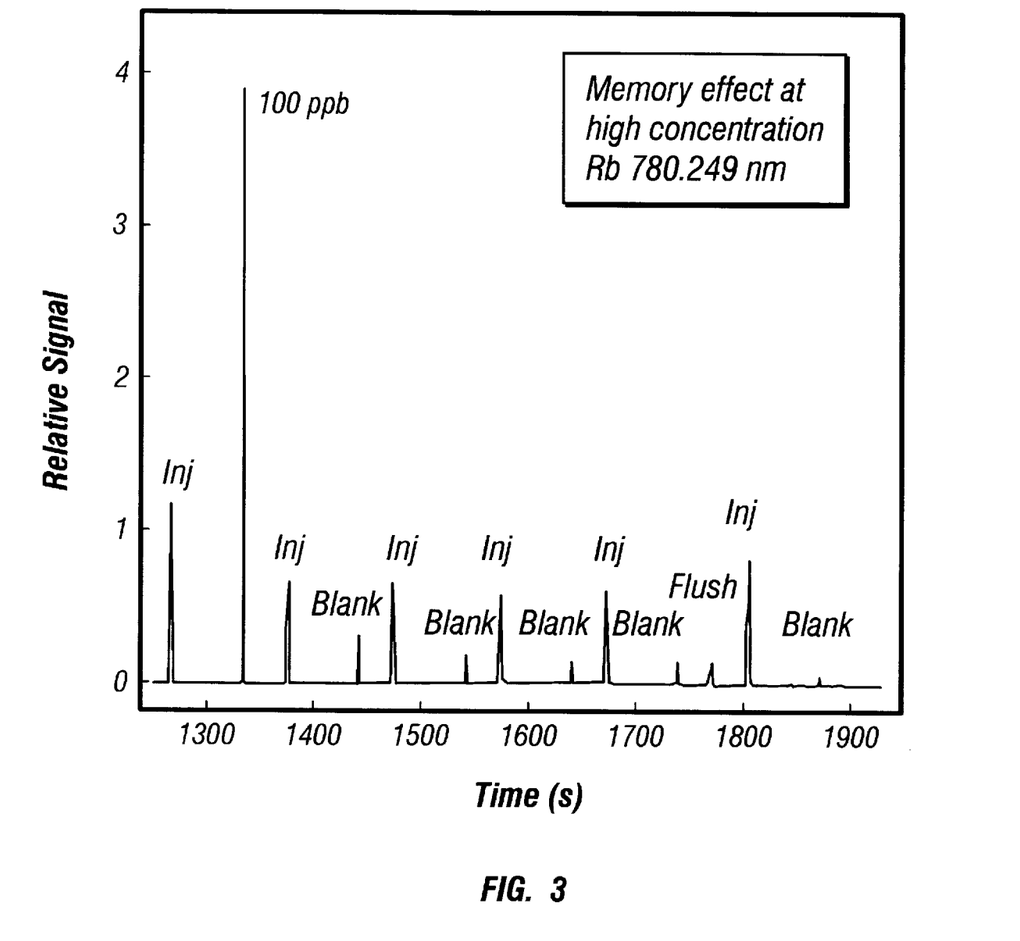
FIGS. 3, 4, and 5 show measured laser wave-mixing signals for Rb solutions by using the spectrometer shown in FIG. 1.

FIG. 3 shows measured laser wave-mixing peaks for a high-concentration 100 ppb Rb injection and the resulting memory effect. At this relatively high concentration level, at least five blank injections may be performed before the next analyte injection in order to eliminate all the residues. A tube flushing procedure ensures elimination of the memory effect as much as possible. The tall injection peaks are recorded when the input laser beams are reflected by the injector arm entering the graphite tube through the injector port.

Figure 4:
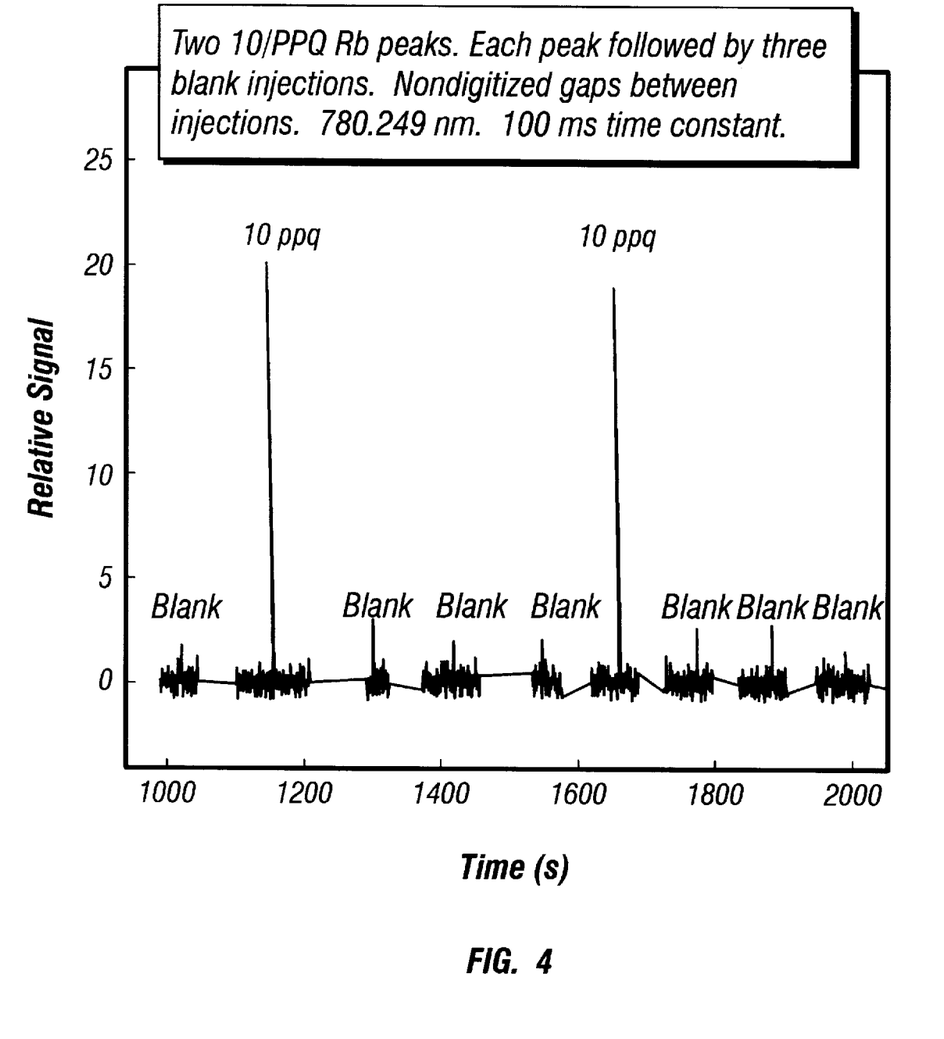

FIG. 4 shows three peaks observed in a 10-parts-per-quadrillion Rb analyte with three blank peaks following each analyte injection. At this lower concentration level, the memory effect is relatively insignificant, and the analyte peaks are still consistently well above the blank peaks. Even at this low concentration range, three blank injections are performed after each analyte injection to ensure that no residues remain from the previous analyte injection. A new graphite tube is used when changing to a new concentration range. For 1 ppq Rb injections, memory effects no longer exist and blank peaks are so small that they are buried under the baseline noise level. At the 1 ppq concentration level, the analyte amount injected is so minute that the normal furnace firing program and the argon flush manage to eliminate any minute analyte residue, and hence, subsequent blank firings show negligible blank peaks.

Figure 5:
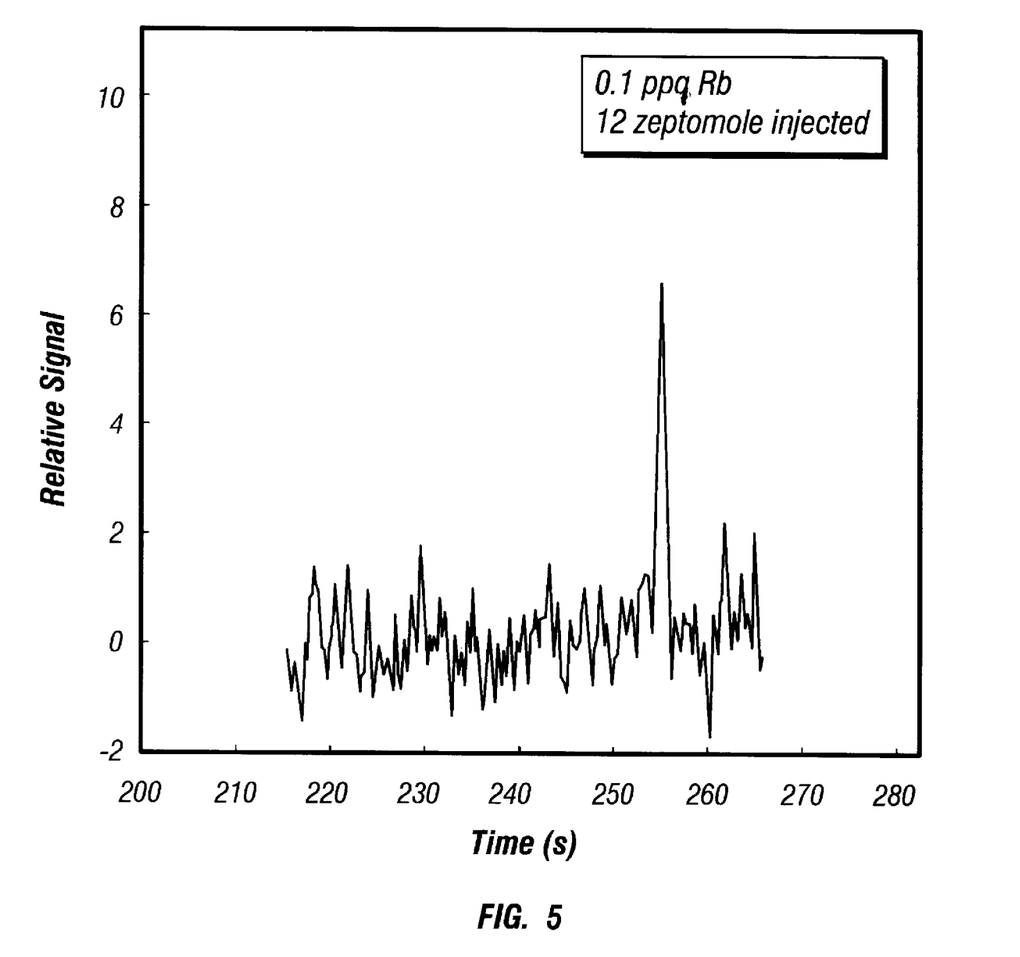

FIG. 5 shows the four-wave-mixing signal peak at 0.1 ppq concentration. This corresponds to a preliminary "injected" mass detection limit of 0.07 ppq, 0.7 attogram or 8 zeptomole (at S/N 2) based on 20 $\mu$L injection (i.e., 10 $\mu$L analyte, 10 $\mu$L blank). Assuming that approximately 15% is lost during the drying, ashing, and atomization stages, and that the laser probe volume is 1% of that of the total analyte population volume produced, one can estimate that only about 60 Rb atoms are present inside the laser cross overlap volume between the two beams that write the wave-mixing gratings. The number of Rb atoms present inside the laser probe volume is even smaller when the short residence time during the atomization stage is considered.

The spectrum in FIG. 5 is recorded by the lock-in amplifier using a 2.5 kHz amplitude modulation frequency with a photodiode and an optical chopper. The preliminary detection limits of 0.07 ppq, 0.7 attogram and 8 zeptomole are encouraging especially since the graphite furnace is not a continuously firing atomizer with a stable atom population, and it has only an atomization time window of about 2 seconds. The detection sensitivity may be improved by other detection techniques such as modulating the wavelength of the laser 102 to turn the wavelength of the beams on and off the resonance wavelength to modulate the intensity of the signal beam or by modulating the polarization of one input beam to modulate the polarization of the signal beam.

Some procedures are found to be effective in enhancing the signal-to-noise ratio in the system. For example, a grounded Faraday cage around the photodetector may be used to substantially reduce the baseline noise level. The use of Teflon wedge O-rings to seal the graphite furnace windows can also significantly reduce the optical background noise. The windows are tilted at an angle to prevent the reflected input beams from retracing back. Micro spatial filters can be used in addition to the alignment templates 120 and 122 to significantly enhance the signal-to-noise ratio since the signal beam (i.e., a laser beam) can be focused very tightly to go through the micro apertures while the background noise is blocked. A wavelength filter may also be used to improve the noise filtering in detecting the signal.

The signal-to-noise ratio can be also improved by positioning the laser overlap probe volume in the top third of the graphite tube (i.e., closer to the top wall of the tube).

Although the wave-mixing signal strength is the same when probing the lower section or the upper section of the graphite tube, the noise levels during the drying and ashing stages are lower when the laser probe volume is positioned in the upper third section of the graphite tube. Since the vaporization of the analyte liquid occurs at the bottom wall of the graphite tube, clusters of small liquid drops produced from the vaporization of the solvent are concentrated near the bottom wall and can scatter the laser beams. Hence, when the laser probe volume is placed near the tube bottom, the scattered background light level is higher than the background light when the laser probe volume is placed near the top of the tube. The position of the overlap probe volume of all the input beams can be adjusted within the tube to improve the signal-to-noise ratio by lowering or raising the graphite tube without disturbing the rest of the laser alignment.

Different types of graphite tubes available commercially have different advantages. Both partition-type and platform-type tubes are found to be effective in the analyzer 100 shown in FIG. 1. The design of the platform-type graphite tube slightly restricts the alignment of the input beams in our non-planar three-dimensional wave-mixing setup. Hence, partition-type graphite tubes with their more open design are used throughout this work for Rb measurements. Proper uses of the graphite tube gas flow and the matrix composition are important since they ensure optimal graphite furnace atomization conditions, removal of analyte and matrix residues, and prevention of rapid tube oxidation.

The four-wave-mixing signal in general has a cubic dependence on the input laser power. The signal strength, and hence, the detection sensitivity can be further enhanced by using higher input beam intensities up to about the saturation intensity. The four-wave-mixing signal also has a quadratic dependence on absorption coefficient. For analytes with low absorption coefficients, the wave-mixing detection sensitivity is still comparable to or better than those of conventional laser methods because of the nonlinear signal properties such as cubic power dependence, virtually 100% optical collection efficiency, and the laser-like coherence properties of the signal beam. For example, unlike laser-induced fluorescence methods where the signal is a small fraction of a widely diffused fluorescence signal laser, the wave-mixing signal is a collimated coherent laser-like beam and hence nearly the entire signal beam can be directed into a photodetector. Furthermore, since wave mixing is an absorption method, both fluorescing and non fluorescing analytes can be measured.

Although only a preferred embodiment has been described, various modifications may be made. For example, different types of diode lasers or other types of lasers (e.g., fiber lasers) may be used. Different types of graphite furnace, various gas-phase, liquid-phase and solid-phase sample cells may also be used. The graphite tube may not be a closed cell but has an opening. An inductively-coupled-plasma (ICP) chamber may be used. Further, optical fibers may be used to transmit the pump and probe beams from the laser to the graphite furnace. These and others are intended to be within the scope of the following claims.

What is claimed is:

1. A device for optical nonlinear four-wave mixing, comprising:

(1) a gas-phase atomizer having an atomizer chamber with a bottom wall and a top wall and operable to vaporize a sample solution received from the bottom wall to produce a sample vapor, the atomizer chamber having a first optical window to receive a probe beam and a first pump beam, and a second optical window opposing the first optical window to receive a second pump beam, wherein the probe beam, the first and second pump beams overlap in the sample vapor to produce a signal beam through a four-wave mixing process in the sample vapor;

(2) first and second alignment templates each having at least three apertures formed on an opaque plate and respectively disposed near the first and second windows of the atomizer chamber to define optical paths for the probe beam, first and second pump beams, and signal beam so that the probe beam forms an acute angle of less than about 20 degrees with the first pump beam and is outside a plane defined by the first and second pump beams, and the probe beam, the first and second pump beams overlap in a location within the atomizer chamber closer to the top wall than the bottom wall, wherein each optical path is determined by one aperture in the first alignment template and another aperture in the second template and the apertures in each alignment template are sized to make a volume formed by the overlapped probe beam, first and second pump beams less than a volume occupied by the sample vapor; and (3) a laser tunable to generate a laser beam at a desired wavelength corresponding to an absorption line in the sample vapor and to produce a total laser intensity approximately equal to a saturation intensity of the absorption line.

2. The device as in claim 1, wherein the first and second alignment templates are symmetrically located with respect to a location where the probe beam, the first and second pump beams overlap and a pattern of the apertures in the first alignment template is a center reverse image of a pattern of the apertures in the second alignment template.

3. The device as in claim 1, further comprising a spatial filter in each optical path to reduce background noise in the signal beam.

4. The device as in claim 1, wherein the laser comprises a diode laser.

5. The device as in claim 4, wherein the diode laser is tunable by adjusting at least one of a temperature and a driving electrical current of the diode laser.

6. The device as in claim 1, wherein the laser comprises a fiber laser.

7. The device as in claim 1, further comprising a photo detector disposed in the optical path of the signal beam to convert the signal beam into an electrical signal and a polarizer having a polarization direction substantially parallel to a polarization of the signal beam to filter light received by the photo detector.

8. The device as in claim 1, wherein the atomizer chamber includes a graphite furnace.

9. The device as in claim 1, wherein the atomizer chamber is configured to vaporize the sample solution by an inductively coupled plasma process.

10. A method for performing spectroscopic measurements by using optical nonlinear four-wave mixing, comprising:

(1) preparing a sample solution that includes particles of a sample to be measured;

(2) injecting the sample solution into an atomizer chamber of a gas-phase atomizer to vaporize the sample solution and to produce a sample vapor;

(3) producing a probe beam, a first pump beam and a second pump beam that are coherent with one another and are in resonance with an absorption transition in the sample;

(4) overlapping the probe beam, the first pump beam, and the second pump beam in the sample vapor within the atomizer chamber to produce a signal beam by optical nonlinear four-wave mixing;

(5) respectively placing first and second alignment templates each having at least three apertures formed on an opaque plate on both sides of the atomizer chamber to define optical paths for the probe beam, first and second pump beams, and signal beam so that the probe beam forms an acute angle of less than about 20 degrees with the first pump beam and is outside a plane defined by the first and second pump beams, and the probe beam, the first and second pump beams overlap in a location within the atomizer chamber closer to the top wall than the bottom wall; and (6) detecting the signal beam to extract spectroscopic information of the sample.

11. The method as in claim 10, further comprising configuring the first and second alignment templates to make a volume formed by the overlapped probe beam, first and second pump beams less than a volume occupied by the sample vapor.

12. The method as in claim 10, further comprising using a laser to produce the probe beam, first and second pump beams.

13. The method as in claim 12, wherein the laser includes a diode laser and is tunable by adjusting at least one of a temperature and a driving electrical current of the diode laser.

14. The method as in claim 12, wherein the laser includes a fiber laser.

15. The method as in claim 10, further comprising using a polarizer that has a polarization direction substantially parallel to a polarization of the signal beam to reduce background noise in detection the signal beam.

16. The method as in claim 10, further comprising injecting a blank solution into the atomizer chamber that is used for the sample solution and does not include particles of the sample before injecting the sample solution, and detecting a signal beam associated with the blank solution as background noise in detecting the signal beam obtained from the sample solution.

17. The method as in claim 10, wherein the preparation of the sample solution includes adding an ionization suppressor in the sample solution to reduce ionization of particles of the sample during vaporization.

18. The method as in claim 10, further comprising keeping a total intensity of the probe beam, first and second pump beams approximately equal to or less than a saturation intensity of the sample.

19. The method as in claim 10, further comprising vaporizing the sample solution by a inductively coupled plasma process.

20. A method for performing spectroscopic measurements by using optical nonlinear four-wave mixing, comprising:

(1) preparing a sample solution that includes particles of a sample to be measured;

(2) injecting the sample solution into an atomizer chamber of a gas-phase atomizer to vaporize the sample solution and to produce a sample vapor;

(3) respectively placing first and second alignment templates each having at least three apertures formed on an opaque plate on both sides of the atomizer chamber to define optical paths for a probe beam, first and second pump beams, and a signal beam so that the probe beam forms an acute angle of less than about 20 degrees with the first pump beam and is outside a plane defined by the first and second pump beams, and the probe beam, the first and second pump beams overlap in a location within the atomizer chamber closer to the top wall than the bottom wall, (4) using an alignment optical beam to produce a probe alignment beam which traces the probe beam, a first pump alignment beam which traces the first pump beam, a second pump alignment beam which traces the second pump beam, and a signal alignment beam which traces the signal beam, to align the first and second alignment templates and other beam guiding elements;

(5) using a laser to produce and direct the probe beam, first and second pump beams in their respective optical paths determined by the first and second alignment templates; and (6) detecting the signal beam to extract spectroscopic information of the sample.

21. The method as in claim 20, further comprising configuring the first and second alignment templates to make a volume formed by the overlapped probe beam, first and second pump beams less than a volume occupied by the sample vapor.

22. The method as in claim 20, further comprising using a polarizer that has a polarization direction substantially parallel to a polarization of the signal beam to reduce background noise in detection the signal beam.

23. The method as in claim 20, further comprising injecting a blank solution into the atomizer chamber that is used for the sample solution and does not include particles of the sample before injecting the sample solution and detecting a signal beam associated with the blank solution as background noise in detecting the signal beam obtained from the sample solution.

24. The method as in claim 20, wherein the preparation of the sample solution includes adding an ionization suppressor in the sample solution to reduce ionization of particles of the sample during vaporization.

25. The method as in claim 20, further comprising keeping a total intensity of the probe beam, first and second pump beams approximately equal to or less than a saturation intensity of the sample.

* * * * *